(12) United States Patent
Neftel

(10) Patent No.: US 10,112,008 B2
(45) Date of Patent: Oct. 30, 2018

(54) MEDICAL DEVICE FOR ADMINISTERING A SOLUTION

(75) Inventor: Fréderic Neftel, Lausanne (CH)

(73) Assignee: DEBIOTECH S.A., Lausanne (CH)

( * ) Notice: Subject to any disclaimer, the term of this patent is extended or adjusted under 35 U.S.C. 154(b) by 1318 days.

(21) Appl. No.: 12/300,740

(22) PCT Filed: Jun. 18, 2007

(86) PCT No.: PCT/IB2007/052329
§ 371 (c)(1),
(2), (4) Date: Dec. 15, 2008

(87) PCT Pub. No.: WO2008/004148
PCT Pub. Date: Jan. 10, 2008

(65) Prior Publication Data
US 2009/0118695 A1     May 7, 2009

(30) Foreign Application Priority Data

Jul. 6, 2006   (EP) .................................... 06116727

(51) Int. Cl.
*A61M 5/168*     (2006.01)
(52) U.S. Cl.
CPC ....... *A61M 5/1684* (2013.01); *A61M 2205/18* (2013.01)
(58) Field of Classification Search
CPC ..................... A61M 2205/18; A61M 5/1684
USPC .................. 604/65, 67, 151, 500, 890.1
See application file for complete search history.

(56) References Cited

U.S. PATENT DOCUMENTS

| | | | |
|---|---|---|---|
| 4,085,046 A * | 4/1978 | Saporito, Jr. .................. | 210/90 |
| 5,681,285 A | 10/1997 | Ford et al. | |
| 6,572,545 B2 * | 6/2003 | Knobbe et al. .............. | 600/365 |
| 2003/0011393 A1 | 1/2003 | Farnworth et al. | |

(Continued)

FOREIGN PATENT DOCUMENTS

| | | |
|---|---|---|
| EP | 1 359 395 | 11/2003 |
| JP | 2002-248167 | 9/2002 |

(Continued)

OTHER PUBLICATIONS

International Search Report for PCT/IB2007/052329, dated Mar. 10, 2008.

(Continued)

*Primary Examiner* — Imani Hayman
(74) *Attorney, Agent, or Firm* — Nixon & Vanderhye P.C.

(57) ABSTRACT

A medical device for administering a solution, the device including a pump, a reservoir, and a communication structure for connecting the reservoir and the pump, and a line for connecting the medical device to the patient, wherein the medical device is adapted to use a mathematical model in order to determine at any moment a physical or chemical characteristics of the solution, which is contained in the reservoir, wherein the mathematical model takes account of a modification of the solution in the reservoir over the course of time as a function of an exposure to temperature, to humidity, or to pressure of the solution, or ageing or permeability of the reservoir; and the medical device is adapted to inform the patient about refilling the solution or changing the reservoir depending on the modification of the characteristics of the solution.

30 Claims, 2 Drawing Sheets

(56) References Cited

U.S. PATENT DOCUMENTS

| | | |
|---|---|---|
| 2003/0020433 A1 | 1/2003 | Knish et al. |
| 2003/0113931 A1* | 6/2003 | Pan et al. .................. 436/113 |
| 2003/0204359 A1* | 10/2003 | Blakley .................. 702/130 |
| 2005/0025644 A1 | 2/2005 | Ford |
| 2005/0177137 A1 | 8/2005 | Kipfer |
| 2005/0277912 A1 | 12/2005 | John |
| 2007/0239096 A1* | 10/2007 | Keenan ............ A61B 5/14532 604/4.01 |
| 2007/0243621 A1* | 10/2007 | Zweig ............ G01N 33/54373 436/83 |

FOREIGN PATENT DOCUMENTS

| | | |
|---|---|---|
| JP | 2004-583 | 1/2004 |
| JP | 2005-537116 | 12/2005 |
| WO | 2005/110515 | 11/2005 |

OTHER PUBLICATIONS

English translation of Written Opinion (IPRP—Chapter I) dated Mar. 10, 2008.
Japanese Office Action dated Mar. 6, 2012 and its English translation.
Japanese Office Action dated Apr. 15, 2014 issued in Japanese Patent Application No. 2009-517510 and English Translation, 10 pp.

\* cited by examiner

US 10,112,008 B2

MEDICAL DEVICE FOR ADMINISTERING A SOLUTION

This application is the U.S. national phase of International Application No. PCT/IB2007/052329, filed 18 Jun. 2007, which designated the U.S. and claims priority to European Application No. 06116727.6, filed 6 Jul. 2006, the entire contents of each of which are hereby incorporated by reference.

FIELD OF THE INVENTION

The present invention applies to the field of administering medical solutions, for example solutions containing insulin.

PRIOR ART

There are several types of medical devices designed for administering a solution. Such devices comprise at least one reservoir communicating with a pump, the whole device being connected to a patient by means of a tube or a subcutaneous, intramuscular or venous access.

The solution contained in the reservoir is generally administered over a certain period of time or at defined intervals.

A problem with the devices of the prior art is that the concentration of the solution may vary over the course of time, on account of the solution being stored in the reservoir. On this point, see the appended graph showing the variation in the insulin concentration over a period of 35 days in a reservoir of the "Topas" type, which comprises on one of its walls a flexible film made of Surlyn on the inside and of Mylar on the outside, the insulin solution being stored at 37° C.

The causes of this variation may be the evaporation experienced by the solution, the stability of the medicament, or any degradation and/or modification of its content.

This phenomenon is all the more pronounced when the reservoir walls are permeable and/or when the solution is administered over a long period of time.

Administration of a solution whose concentration and/or characteristics vary over the course of time may cause complications or even pose a threat to the treatment or health of the patient.

There is therefore a need to remedy the aforementioned problems.

DESCRIPTION OF THE INVENTION

The present invention represents an improvement over the devices of the prior art.

Figure 1:
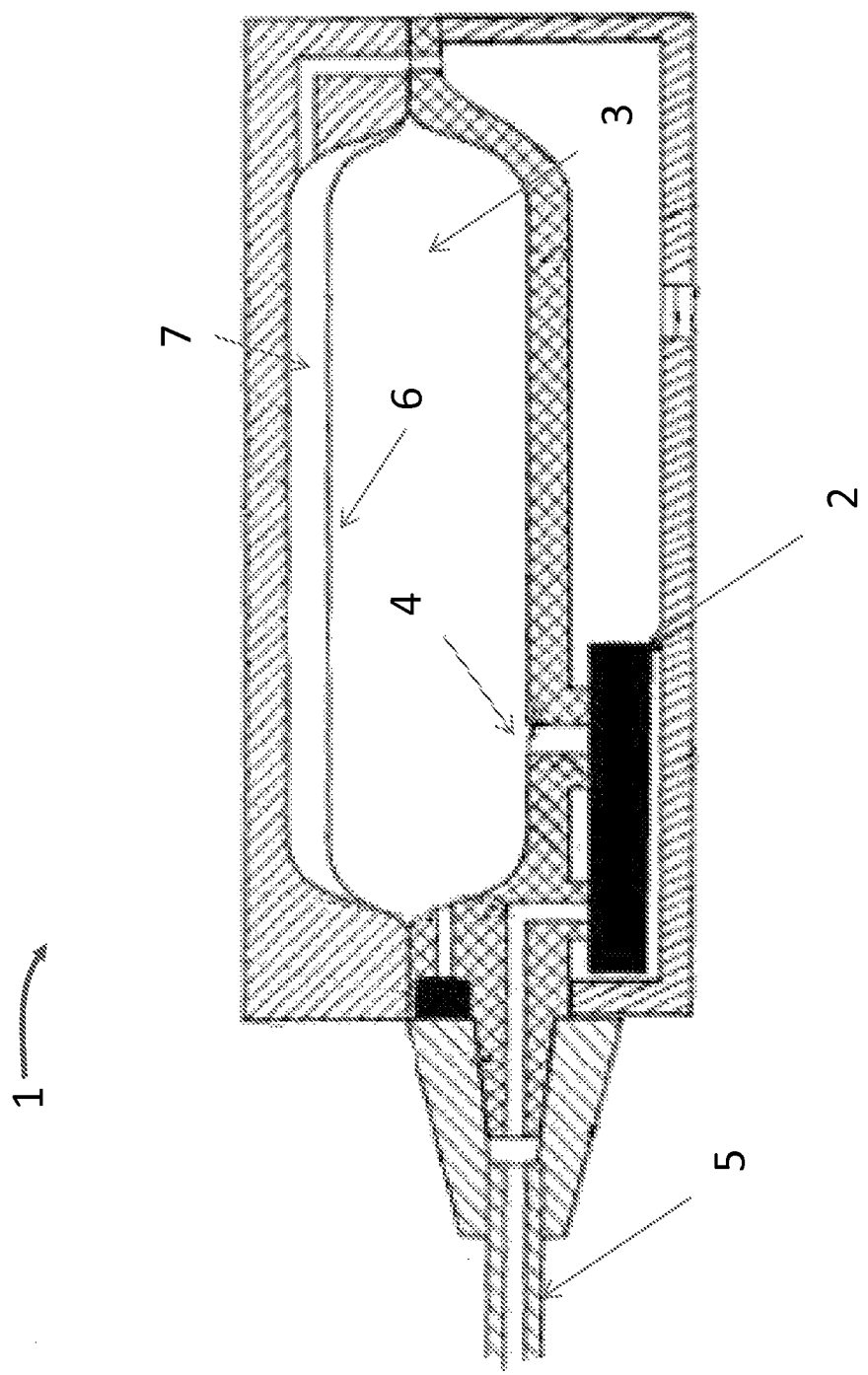
FIG. 1 shows a possible embodiment of the invention.
Figure 2:
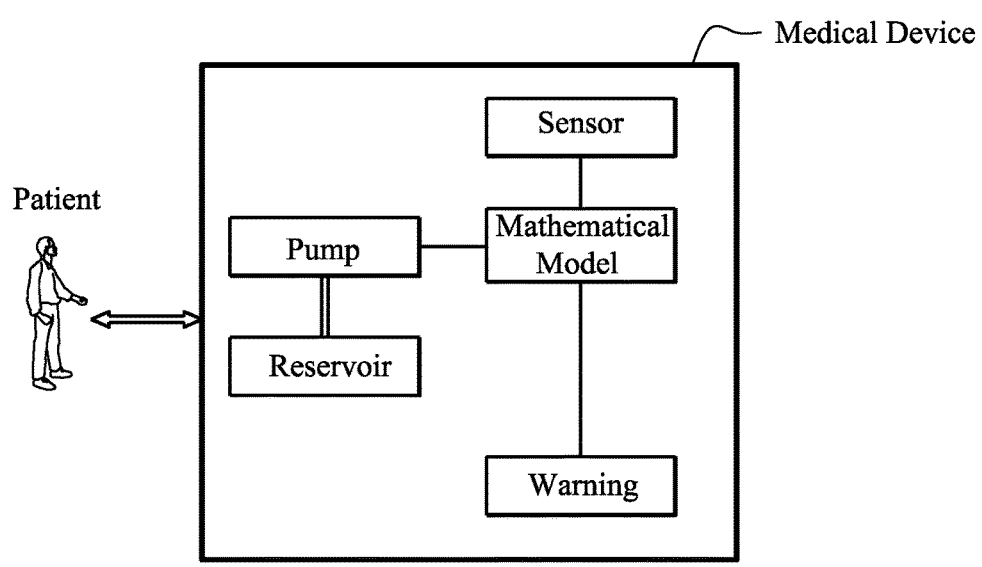
FIG. 2 shows elements of a possible embodiment of the invention.

In the invention, for example, an embodiment as depicted in reference to FIG. 1, the solution to the aforementioned problem lies in a medical device (1) for administering a solution, said device (1) comprising pumping means (a pump) (2), a reservoir (3), means of communication (4) between said reservoir and said pumping means (also known as a line for connecting the reservoir and the pumping means), and a line (5) for connecting the medical device to a patient. The device according to the invention is characterized in that it comprises means for determining the physical/chemical characteristics of the solution as a function of time by means of a mathematical model that takes account of the permeability of the reservoir walls (6) as a function of time and the temperature of the solution.

According to one embodiment of the invention, the device comprises means for varying the administration of the solution as a function of a variation in the concentration of the solution determined by means of the mathematical model.

Advantageously, the mathematical model can take account in particular of the characteristics of evaporation, absorption, adsorption or any other modification of the solution over the course of time as a function of the exposure to temperature, to humidity, to pressure and to any other condition of use, and, if appropriate, the ageing and/or deterioration of the reservoir over the course of time. Thus, the characteristics of the solution can be calculated at any moment as a function of this mathematical model.

Once the characteristics of the solution are modified, it is desirable to take account of this in the mode of administration of the solution, in order to ensure effective and reliable administration.

The modification may in particular involve evaporation, over the course of time, of water through a flexible membrane (7) constituting the reservoir, the consequence of which is to increase the concentration of the active principle in the solution. In this case, failure to correct the concentration would have the effect of causing an overdose of the medicament administered. The principle of the invention is to correct the administration of the solution in order to ensure an at all times effective quantity of active principle by using the mathematical model to take into account the effective concentration of the solution over the course of time and to adapt the flow rate as a consequence. As this evaporation often depends on the temperature, it may be useful also to integrate into the mathematical model the effect of exposure to temperature over the course of time, in order to be able to more precisely predict the probable concentration of the solution at a given moment. To do so, it is necessary to provide a temperature sensor, preferably operating continuously, the mathematical model being able to integrate the calculation of the evaporation over the course of time according to a model that can be nonlinear.

It may also be useful to use the mathematical model in order to predict at any moment the quantity of certain substances contained in the reservoir, such as preservatives (meta-cresol, phenol) that are very often used in combination with certain medical substances (insulin for example). If the content of some of these substances is no longer sufficient, it may be useful to warn the user that refilling of the reservoir is necessary or that the reservoir has to be changed. As some of these substances are very volatile, they have a tendency to be the first to diminish in the reservoir (e.g. phenol).

According to one embodiment of the invention, it may be useful to measure certain parameters of the solution, the development of which parameters may serve as an indicator to the mathematical model to correct the calculation of the characteristics of the solution. This parameter may, for example, be the conductivity of the solution, which is a good indicator of evaporation of water over the course of time.

According to one embodiment of the invention, the user is able to continuously read off information relating to the characteristics of the solution contained in the reservoir. Such an indication may, for example, be representative of the quality of the solution (Excellent, Average, Borderline), in order to give the user advance warning about refilling the solution and/or changing the reservoir. An indication of this kind is very different than the only indication nowadays available on administration devices, namely the residual volume of the solution, and offers the user a greater degree of safety.

The present invention affords a number of advantages, in particular that of ensuring at any time that the dose administered to the patient is as correct as possible, taking account the foreseeable modifications in the characteristics of the solution over the course of time. It also ensures that, when the conditions of efficacy and/or safety are no longer guaranteed, the user is alerted and the reservoir is changed or refilled in time. Finally, it also allows the user to be given sufficient advance warning of the need to refill or change the reservoir.

In the event of a refilling of the reservoir, it may also be important to take account of the possible residual volume of solution present at the time of the refilling (in the case where this residual solution is not emptied), in order to correct the characteristics of the new solution obtained after refilling as a function of the dilution between the old and new solution, the aim again being to ensure improved efficacy and safety in the administration of the solution to the patient.

The graph appended to the present description shows the development in the concentration of various components of an insulin solution U100 (Novorapid) over the course of time in a reservoir comprising a rigid part made of Topas 8007S-04 from Topas Advanced Polymers GmbH and a flexible film made of Surlyn 1702 (30 μm) on the inside and of Mylar D820 (12 μm) on the outside, the two materials being from DuPont, and the solution being maintained at constant temperature (37° C.) for 35 days.

The results observed over the course of timer as a function of temperature, relative to the concentration of insulin and of the different preservative agents are also indicated in the following tables under different evaluation conditions:

A) Study of insulin U100 Novorapid in 3 different bags over 4 weeks at 35° C. with and without vibration of the bag.

|  | Total water loss (%) | | | | |
|---|---|---|---|---|---|
| Type of bag | 1 | 3 | 4 | Mean | Standard deviation |
| Water (total weight) | 2.132 | 1.985 | 2.116 | | |
| 02.06.2006 | 95% | 95% | 94% | 94% | 1% |
| 09.06.2006 | 93% | 93% | 91% | 92% | 1% |
| 16.06.2006 | 91% | 91% | 89% | 90% | 1% |
| 23.06.2006 | 89% | 89% | 86% | 88% | 1% |
| Phenol | | | | | |
| 02.06.2006 | 99% | 97% | 99% | 98% | 1% |
| 09.06.2006 | 97% | 96% | 101% | 98% | 3% |
| 16.06.2006 | 98% | 98% | 100% | 99% | 1% |
| 23.06.2006 | 97% | 97% | 99% | 98% | 1% |
| m-Cresol | | | | | |
| 02.02.2006 | 87% | 85% | 87% | 86% | 1% |
| 09.06.2006 | 81% | 80% | 84% | 81% | 2% |
| 16.06.2006 | 75% | 74% | 78% | 76% | 2% |
| 23.06.2006 | 68% | 69% | 71% | 69% | 2% |
| Insulin | | | | | |
| 02.02.2006 | 103% | 102% | 105% | 103% | 2% |
| 09.06.2006 | 109% | 106% | 109% | 108% | 2% |
| 16.06.2006 | 111% | 110% | 114% | 112% | 2% |
| 23.06.2006 | 119% | 117% | 123% | 120% | 3% |

B) Study of insulin U100 Novorapid in 5 different bags (A, B, D, E and F) over 1 to 6 weeks at different temperatures (4° C. and 35° C.) with (vibr) and without (still) vibration of the bag, in comparison with insulin contained in a carpule (cartridge):

| Sample No | Type | M-Scan No | Date exp | [° C.] Temp | Condition | [weeks] Duration | [number] Fibrils | Phenol | Cresol | Insulin | [g] Initial weight |
|---|---|---|---|---|---|---|---|---|---|---|---|
| 1 | B | 16989 | October 2003 | 4 | still | 1 | | 91% | 78% | 100% | |
| 2 | B | | October 2003 | 4 | still | 1 | 0.02 | | | | 7.80 |
| 3 | D | 16990 | March 2003 | 4 | still | 1 | 0.00 | 93% | 85% | 99% | 8.29 |
| 4 | cartridge | 16991 | October 2003 | 4 | still | 1 | 0.00 | 100% | 100% | 100% | 8.52 |
| 5 | B | 16992 | October 2003 | 35 | still | 1 | 0.01 | 73% | 52% | 93% | 7.66 |
| 6 | B | 16993 | October 2003 | 35 | still | 1 | 0.04 | 72% | 50% | 93% | 7.62 |
| 7 | D | 16994 | March 2003 | 35 | still | 1 | 0.01 | 46% | 18% | 98% | 7.96 |
| 8 | cartridge | 16995 | October 2003 | 35 | still | 1 | 0.02 | | | | 8.53 |
| 9 | B | 16996 | October 2003 | 35 | vibr | 1 | 0.01 | | | | 7.41 |
| 10 | B | 16997 | October 2003 | 35 | vibr | 1 | 0.01 | | | | 7.82 |
| 11 | D | 16998 | March 2003 | 35 | vibr | 1 | 0.02 | | | | 8.29 |
| 12 | cartridge | 16999 | October 2003 | 35 | vibr | 1 | 0.00 | | | | 8.47 |
| 13 | B | 17054 | October 2003 | 4 | still | 2 | 0.00 | | | | 7.56 |
| 14 | B | 17055 | October 2003 | 4 | still | 2 | −0.01 | | | | 7.51 |
| 15 | D | 17056 | March 2003 | 4 | still | 2 | 0.00 | | | | 8.41 |
| 16 | cartridge | 17057 | October 2003 | 4 | still | 2 | 0.00 | | | | 8.49 |
| 17 | B | 17058 | October 2003 | 35 | still | 2 | 0.00 | | | | 7.45 |
| 18 | B | 17059 | October 2003 | 35 | still | 2 | 0.00 | | | | 7.54 |
| 19 | D | 17060 | March 2003 | 35 | still | 2 | −0.01 | 33% | 11% | 94% | 7.98 |
| 20 | cartridge | 17061 | October 2003 | 35 | still | 2 | 0.01 | | | | 8.50 |
| 21 | B | 17062 | October 2003 | 35 | vibr | 2 | −0.01 | | | | 7.65 |
| 22 | B | 17063 | October 2003 | 35 | vibr | 2 | −0.01 | | | | 7.46 |
| 23 | D | 17064 | March 2003 | 35 | vibr | 2 | −0.01 | | | | 8.44 |
| 24 | cartridge | 17065 | October 2003 | 35 | vibr | 2 | 0.02 | | | | 8.52 |
| 25 | B | | March 2003 | 4 | still | 4 | −0.01 | | | | 7.69 |
| 26 | B | | March 2003 | 4 | still | 4 | 0.05 | | | | 7.63 |
| 27 | cartridge | | October 2003 | 4 | still | 4 | 0.02 | | | | 8.53 |
| 28 | B | | March 2003 | 35 | still | 4 | 0.03 | | | | 7.53 |
| 29 | B | | March 2003 | 35 | still | 4 | 0.05 | | | | 7.59 |
| 30 | D | | March 2003 | 35 | still | 4 | 0.05 | | | | 7.97 |
| 31 | cartridge | | October 2003 | 35 | still | 4 | 0.05 | | | | 8.51 |
| 32 | B | | March 2003 | 35 | vibr | 4 | 0.06 | | | | 7.67 |
| 33 | B | | March 2003 | 35 | vibr | 4 | 0.05 | | | | 6.99 |
| 34 | D | | March 2003 | 35 | vibr | 4 | 0.06 | | | | 8.22 |

-continued

| Sample No | Type | M-Scan No | Date exp | [° C.] Temp | Condition | [weeks] Duration | [number] Fibrils | Phenol | Cresol | Insulin | [g] Initial weight |
|---|---|---|---|---|---|---|---|---|---|---|---|
| 35 | cartridge | | October 2003 | 35 | vibr | 4 | 0.04 | | | | 8.55 |
| 36 | B | | March 2003 | 4 | still | 6 | | | | | 7.52 |
| 37 | B | | March 2003 | 4 | still | 6 | | | | | 7.54 |
| 38 | cartridge | | October 2003 | 4 | still | 6 | | | | | 8.53 |
| 39 | B | | March 2003 | 4 | still | 6 | | | | | 7.76 |
| 40 | B | | March 2003 | 35 | still | 6 | | | | | 7.62 |
| 41 | cartridge | | October 2003 | 35 | still | 6 | | | | | 8.51 |
| 42 | B | | March 2003 | 35 | vibr | 6 | | | | | 7.76 |
| 43 | B | | March 2003 | 35 | vibr | 6 | | | | | 7.69 |
| 44 | cartridge | | October 2003 | 35 | vibr | 6 | | | | | 8.52 |
| 101 | A | 17021 | | 4 | still | 1 | | | | | |
| 102 | E | 17022 | | 4 | still | 1 | | | | | |
| 104 | cartridge | 17023 | | 4 | still | 1 | | | | | |
| 105 | A | 17024 | | 35 | still | 1 | | | | | |
| 106 | E | 17025 | | 35 | still | 1 | | | | | |
| 107 | F | 17026 | | 35 | still | 1 | | | | | |
| 108 | cartridge | 17027 | | 35 | still | 1 | | | | | |
| 109 | A | 17028 | | 35 | vibr | 1 | | 95% | 84% | 92% | |
| 110 | E | 17029 | | 35 | vibr | 1 | | | | | |
| 111 | F | 17030 | | 35 | vibr | 1 | | 95% | 89% | 92% | |
| 112 | cartridge | 17031 | | 35 | vibr | 1 | | | | | |
| 113 | A | 17032 | | 4 | still | 2 | | | | | |
| 114 | E | 17033 | | 4 | still | 2 | | | | | |
| 116 | cartridge | 17034 | | 4 | still | 2 | | | | | |
| 117 | A | 17035 | | 35 | still | 2 | | 100% | 89% | 104% | |
| 118 | E | 17036 | | 35 | still | 2 | | | | | |
| 119 | F | 17037 | | 35 | still | 2 | | 99% | 87% | 86% | |
| 120 | cartridge | 17038 | | 35 | still | 2 | | | | | |
| 121 | A | 17039 | | 35 | vibr | 2 | | | | | |
| 122 | E | 17040 | | 35 | vibr | 2 | | | | | |
| 123 | F | 17041 | | 35 | vibr | 2 | | | | | |
| 124 | cartridge | 17042 | | 35 | vibr | 2 | | | | | |
| 125 | A | 17043 | | 4 | still | 4 | 0.00 | | | | |
| 126 | E | 17044 | | 4 | still | 4 | 0.00 | | | | |
| 127 | F | | | 4 | still | 4 | | | | | |
| 128 | cartridge | 17045 | | 35 | still | 4 | −0.01 | | | | |
| 129 | A | 17046 | | 35 | still | 4 | 0.01 | 109% | 92% | 113% | |
| 130 | E | 17047 | | 35 | still | 4 | 0.00 | | | | |
| 131 | F | 17048 | | 35 | still | 4 | 0.00 | 104% | 90% | 104% | |
| 132 | cartridge | 17049 | | 35 | still | 4 | 0.01 | | | | |
| 133 | A | 17050 | | 35 | vibr | 4 | 0.00 | | | | |
| 134 | E | 17051 | | 35 | vibr | 4 | −0.01 | | | | |
| 135 | F | 17052 | | 35 | vibr | 4 | 0.00 | | | | |
| 136 | cartridge | 17053 | | 35 | vibr | 4 | 0.01 | | | | |
| 137 | A | 17638 | | 4 | still | 6 | 0.05 | 92% | 81% | 100% | |
| 138 | E | | | 4 | still | 6 | 0.01 | | | | |
| 139 | F | 17637 | | 4 | still | 6 | 0.05 | 95% | 88% | 98% | |
| 140 | cartridge | 17638 | | 4 | still | 6 | | | | | |
| 141 | A | | | 35 | still | 6 | 0.04 | | | | |
| 142 | E | | | 35 | still | 6 | 0.11 | | | | |
| 143 | F | | | 35 | still | 6 | 0.07 | | | | |
| 144 | cartridge | | | 35 | still | 6 | | | | | |
| 145 | A | 17639 | | 35 | vibr | 6 | 0.05 | 94% | 76% | 100% | |
| 146 | E | | | 35 | vibr | 6 | 0.08 | | | | |
| 147 | F | 17640 | | 35 | vibr | 6 | 0.09 | 93% | 81% | 106% | |
| 148 | cartridge | 17641 | | 35 | vibr | 6 | | | | | |

The invention claimed is:

1. A medical device for administering a solution, said device comprising:
   a pump that is not inside a patient,
   a reservoir that is not inside the patient, and
   a communication structure for connecting said reservoir and said pump, wherein said communication structure is not inside the patient, and
   a line for connecting the medical device to the patient,
   a sensor for measuring an exposure of the solution, which is contained in the reservoir, to temperature, to humidity, or to pressure of the solution, or ageing or permeability of the reservoir, over the course of time,
   wherein the medical device uses a mathematical model in order to determine at any moment physical or chemical characteristics of the solution, which is contained in the reservoir, wherein the mathematical model takes account of a modification of the solution in the reservoir over the course of time as a function of an exposure to temperature, to humidity, or to pressure of the solution, or ageing or permeability of the reservoir; and
   wherein the medical device informs the patient about refilling the solution or changing the reservoir depending on the modification of the characteristics of the solution.

2. The device as claimed in claim 1, wherein the mathematical model takes account of the exposure to temperature of the solution.

3. The device as claimed in claim 1, wherein the reservoir has walls and the mathematical model takes account of the permeability of the walls.

4. The device as claimed in claim 1, wherein the mathematical model takes account of the exposure to humidity of the solution.

5. The device as claimed in claim 1, wherein the mathematical model takes account of the exposure to pressure of the solution.

6. The device as claimed in claim 1, wherein the mathematical model takes account of the ageing or deterioration of the reservoir over the course of time.

7. The device as claimed in claim 1, wherein the mathematical model takes account of the exposure to temperature, to humidity, or to pressure of the reservoir over the course of time.

8. The device as claimed in claim 1, wherein the medical device is further adapted to vary the administration of the solution as a function of a variation in the concentration of the solution determined by the mathematical model.

9. The device as claimed in claim 1, comprising a temperature sensor for regularly measuring the temperature of the solution, said medical device being functionally connected to said temperature sensor for continuously measuring the temperature.

10. The device as claimed in claim 1, wherein said mathematical model takes account of the degradation of the solution as a function of time or temperature.

11. The device as claimed in claim 10, wherein the medical device is further adapted to vary the administration of the solution as a function of the concentration of non-degraded active substance contained in the reservoir.

12. The device as claimed in claim 1, wherein the mathematical model is designed to determine the variation in the new concentration of the solution after each refilling of the reservoir as a function of the residual volume of the solution and the refilling volume of the new solution.

13. The device as claimed in claim 1, wherein the mathematical model is designed to determine the characteristics of the solution after each refilling of the reservoir.

14. The device as claimed in claim 1, wherein said sensor measures a conductivity or resistance of the solution, a pH or any other physical parameter of the solution.

15. The device as claimed in claim 1, wherein the medical device is adapted to warn the patient when the solution contained in the reservoir is estimated to no longer correspond to the treatment requirements.

16. The device as claimed in claim 15, wherein the warning is adapted to alert the patient to the fact that the reservoir has to be refilled.

17. The device as claimed in claim 1, wherein the medical device is adapted to warn the patient when the temperature of the solution contained in the reservoir has exceeded a defined threshold during a minimal duration.

18. The device as claimed in claim 1, wherein the medical device is adapted to warn the patient based on a function of the mathematical model that takes account of the temperature to which the solution is exposed at each instant and also of the duration of this exposure.

19. The device as claimed in claim 1, comprising the reservoir designed to contain insulin.

20. The device as claimed in claim 1, wherein the reservoir comprises at least one membrane not totally impermeable to water vapor or to certain components of the solution.

21. The device as claimed in claim 1, wherein the medical device is adapted for indicating the time remaining for possible use of the solution under the current or foreseeable conditions of use.

22. The device as claimed in claim 1, wherein the medical device is designed to inform the patient of the quality of the solution in a way allowing the patient to anticipate a change or refilling in advance.

23. The device as claimed in claim 1, wherein the mathematical model takes account whether the reservoir is vibrated or not.

24. A medical device for administering a solution, said device comprising:
a pump that is not inside a patient,
a reservoir that is not inside the patient,
a communication structure for connecting said reservoir and said pump, and wherein the communication structure is not inside the patient,
a line for connecting the medical device to the patient, and
a sensor for measuring an exposure of the solution, which is contained in the reservoir, to temperature over a course of time,
wherein the medical device uses a mathematical model in order to determine at any moment physical or chemical characteristics of the solution wherein the mathematical model takes account of the data of exposure of the solution to temperature, and
wherein the medical device informs the patient about refilling the solution or changing the reservoir depending on the modification of the characteristics of the solution.

25. The device as claimed in claim 24, wherein the medical device is adapted for estimating the development of certain physical or the chemical characteristics of the solution as a function of time.

26. The device as claimed in claim 24, wherein the medical device is adapted for preventing the administration of the solution when certain physical or chemical characteristics are estimated to have been modified beyond certain acceptable limits.

27. The device as claimed in claim 26, wherein the medical device is adapted for preventing the administration of the solution when the physical or the chemical characteristics no longer correspond to the pharmacopeia defined for said solution.

28. A medical device for administering a solution, said device comprising:
a pump that is not inside a patient,
a reservoir that is not inside the patient,
a communication structure for connecting said reservoir and said pump, and wherein the communication structure is not inside the patient,
a line for connecting the medical device to the patient, and
a sensor for measuring an exposure of the solution, which is contained in the reservoir, to temperature over a course of time,
wherein the medical device uses a mathematical model in order to predict a concentration of an active principle in the solution at a given moment wherein the mathematical model takes account of the data of exposure of the solution to temperature, and
wherein the medical device informs the patient as a function of the mathematical model that takes into account the temperature to which the solution has been exposed at each instant and also the duration of this exposure.

29. The device as claimed in claim 28, wherein the mathematical model takes account whether the reservoir is vibrated or not.

30. A medical device for administering a solution, the device comprising:
- a pump that is not inside a patient;
- a container that is not inside the patient;
- a communication structure between the reservoir and the pump, the communication structure is not inside the patient; and
- a line for connecting the medical device to the patient,
- a sensor for measuring an exposure of the solution, which is contained in the reservoir, to temperature, to humidity, or to pressure of the solution, or ageing or permeability of the reservoir, over the course of time,
- wherein the medical device uses a mathematical model to estimate at different moments physical or chemical characteristics of the solution, which is located in the reservoir, the mathematical model takes account of a modification of the solution in the reservoir over a course of time as a function of an exposure to temperature, to humidity, or to pressure of the solution, or ageing or permeability of the reservoir, and
- wherein the medical device informs the patient about refilling the solution or changing the reservoir and to prevent the administration of the solution when certain physical or chemical characteristics are estimated to be modified beyond acceptable limits.

* * * * *